United States Patent [19]
Snyder et al.

[11] Patent Number: 4,889,679
[45] Date of Patent: Dec. 26, 1989

[54] EDDY CURRENT PROBE APPARATUS HAVING AN EXPANSIBLE SLEEVE

[75] Inventors: David A. Snyder, North Huntingdon; Johnny J. Anderson, Hampton Township, Allegheny County, both of Pa.

[73] Assignee: Westinghouse Electric Corp., Pittsburgh, Pa.

[21] Appl. No.: 156,494

[22] Filed: Feb. 16, 1988

[51] Int. Cl.[4] .............................................. G21C 17/00
[52] U.S. Cl. ................................... 376/258; 324/207; 324/226; 29/157.4
[58] Field of Search ............... 376/258, 245, 252, 260; 29/723, 727, 157.3 C, 157.4, 523, 906; 324/207, 208, 219, 220, 226, 236, 239

[56] References Cited

U.S. PATENT DOCUMENTS

| | | |
|---|---|---|
| 2,622,126 | 12/1952 | Bender et al. . |
| 4,063,157 | 12/1977 | Lorenzi et al. . |
| 4,087,748 | 5/1978 | Pigeon et al. . |
| 4,159,564 | 7/1979 | Cooper, Jr. . |
| 4,195,390 | 4/1980 | Amen . |
| 4,303,884 | 12/1981 | Malick . |
| 4,513,497 | 4/1985 | Finch . |
| 4,513,506 | 4/1985 | Vogeleer . |
| 4,586,249 | 5/1986 | Costlow et al. . |
| 4,616,392 | 10/1986 | Snyder . |
| 4,649,492 | 3/1987 | Sinha et al. . |
| 4,649,493 | 3/1987 | Castner et al. . |
| 4,797,613 | 1/1989 | Wentzell ............................ 324/220 |
| 4,804,291 | 2/1989 | Everett ............................... 403/287 |
| 4,814,702 | 3/1989 | Driggers et al. .................... 324/207 |

*Primary Examiner*—Daniel Wasil
*Attorney, Agent, or Firm*—Walter S. Stevens

[57] ABSTRACT

Eddy current probe apparatus having an expansible sleeve thereon capable of hydraulically diametrically expanding a tubular member into engagement with an adjacent structure and capable of hydraulically diametrically expanding a tubular sealing member disposed in the tubular member into engagement with the interior wall of the tubular member, which probe is capable also of detecting the location of the structure and the extent of diametrical expansion of the sealing member and tubular member. The apparatus comprises a support body, expansion means sealingly attached to and surrounding the support body for diametrically expanding the tubular member or sealing member, and electromagnetic means connected to the support body for continuously electromagnetically detecting the variations in the electromagnetic characteristics of the tubular member, sealing member, and structure and the extent of diametrical expansion of the tubular member and sealing member.

14 Claims, 7 Drawing Sheets

EDDY CURRENT PROBE APPARATUS HAVING AN EXPANSIBLE SLEEVE

BACKGROUND OF THE INVENTION

This invention generally relates to expansion of tubular members and more particularly relates to an eddy current probe apparatus having an expansible sleeve thereon capable of hydraulically diametrically expanding a tube into engagement with a tube sheet or tube support plate and capable of hydraulically diametrically expanding a tubular sealing member into engagement with the interior wall of the tube, which probe is also capable of detecting the location of the tube sheet or support plate and the extent of diametrical expansion of the sealing member and tube.

It is well known that in a nuclear reactor power plant a steam generator generates steam when heat is transferred by conduction from a radioactive primary fluid to a non-radioactive secondary fluid through a heat conductor boundary separating the primary fluid from the secondary fluid. As the temperature of the secondary fluid increases, the secondary fluid reaches saturation temperature beyond which saturation temperature increasing fractions of the secondary fluid enter the vapor phase thereby producing steam. The steam generator typically includes a plurality of tubes through which the primary fluid flows. The walls of these tubes function as the heat conductor boundary for conducting heat from the primary fluid to the secondary fluid. Typically, each tube is supported along its length by a plurality of tube support plates having holes therein for receiving each tube. Moreover, the ends of each tube are typically supported by a tube sheet having apertures therein for receiving each tube. The terminal ends of each tube are typically attached to the tube sheet by welding. As discussed below, although the support plates and tube sheet provide support for each tube, a gap may exist in the hole at the interface of the tube and support plate or in the aperture at the interface of the tube and tube sheet. Thus, a gap may exist between the tube and the support plate or between the tube and the tube sheet.

As indicated above, the primary fluid flowing in the steam generator tubes is radioactive; hence, the steam generator is designed such that the radioactive primary fluid does not radioactively contaminate the secondary fluid by mingling with the secondary fluid. It is therefore desirable that the tubes remain leak-tight so that radioactive primary fluid remains everywhere separated from the secondary fluid to avoid mingling the radioactive primary fluid with the secondary fluid.

Occasionally, due to vibration and tube wall intergranular cracking caused by stress and corrosion during operation, the steam generator tubes may develop surface and volume flaws and thus may not remain leak-tight. If through-wall cracking occurs due to the flaws, the radioactive primary fluid may mingle with the secondary fluid. The through-wall cracking may occur in a tube portion adjacent the gap due to tube vibration and intergranular stress corrosion cracking at that location. As explained presently, these gaps between the tube and the support plate or between the tube and the tube sheet may lead to deterioration of the tube at the location adjacent the gap due to flow induced vibration of the tube against the support plate or tube sheet thus wearing the tube and due to deposition of contaminates within the gap thus constricting, stressing and corroding the tube. Hence, precautionary measures may be necessary to ensure that surface and volume flaws caused by vibration, stress and corrosion do not develop in the tubes so that mingling of the radioactive primary fluid with the secondary fluid is avoided. It would be desirable to provide an apparatus to expand the tube having flaws therein into engagement with the tube sheet or with the support plate so that the gap is closed or to sleeve the tube having the flaws.

However, before the tube may be expanded to close the gap, the location of the support plate or tube sheet should first be precisely determined so that the tube may be precisely diametrically expanded against the support plate or tube sheet. Moreover, it is desirable that the extent of diametrical expansion of the tube be precisely continuously monitored so that the tube suitably closes the gap or so that the tube is suitably sleeved in a predetermined manner. However, one problem in the art has been to provide an eddy current device for precisely determining the location of the support plate or tube sheet and for determining the diametrical expansion of the tube. Moreover, because it may be desirable to use hydraulic means to expand the tube, yet another problem in the art has been to provide an eddy current device capable of resisting the relatively high pressures experienced by the eddy current device in the instance when the tube is hydraulically expanded.

There are several eddy current probe devices known in the art for expanding tubular members. One such device is disclosed by U.S. Pat. No. 4,159,564 issued July 3, 1979 in the name of Frank W. Cooper, Jr. entitled "Mandrel for Hydraulically Expanding a Tube into Engagement with a Tubesheet" and assigned to the Westinghouse Electric Corporation. The Cooper, Jr. patent is directed towards hydraulically expanding tubes in a tube sheet of a heat exchanger and comprises a mandrel with an eddy current coil for detecting the inner edge of a tube sheet. The mandrel further includes a body portion having a leading and trailing end. The body portion has an elongated groove in each end thereof and an elastomer sealing member disposed in each groove. The mandrel also includes passages disposed in the trailing end for introducing pressurized fluid between the grooves, whereby the pressurized fluid is contained between the sealing members, the mandrel, and the tube to hydraulically expand the tube into engagement with the tube sheet without using an expansible sleeve. The eddy current coil is connected to the mandrel at the leading end on the out-board side of the grooves. However, the Cooper, Jr. patent does not appear to disclose an eddy current probe apparatus having an expansible sleeve for expanding a tube into engagement with a tube sheet or tube support plate.

Another eddy current probe device capable of expansibly engaging a tube for inspecting the tube for flaws is disclosed by U.S. Pat. No. 4,303,884 issued Dec. 1, 1981 in the name of Franklin S. Malick entitled "Inflatable Eddy Current Inspection Probe for Inspection of Tubular Means" and assigned to the Westinghouse Electric Corporation. This patent discloses a device comprising a plurality of axially oriented plastic strips which form the circumference of the probe with each plastic strip having mounted thereon an eddy current coil. A rubber tube is disposed on the interior of the plastic strips so that when the rubber tube is inflated, the plastic strips and coils are forced outward into close contact with the tube so that the eddy current coils can detect flaws in the tube. Although the Malick patent may disclose an inflatable eddy current inspection probe, the Malick patent does not appear to disclose an eddy current probe having a cylindrical sleeve capable of expanding a tube into engagement with a tube sheet or support plate in the manner of the present invention.

A device for expanding tubular members is disclosed by U.S. Pat. No. 4,195,390 issued Apr. 1, 1980 in the name of Randall M. Amen and entitled "Apparatus and Method for Manipulation and Sleeving of Tubular Members". The Amen device includes a hollow, elastic, tubular bladder held on an elongate connection member or tie rod sealably positioned therewithin by means of a pair of end caps with means for providing fluid communication to the sealed interior of the bladder. With the expansion apparatus positioned within a tubular member and hydraulic fluid pumped into the bladder, the bladder will expand the tubular member beyond its elastic limit. Although the Amen patent may disclose a device having a tubular bladder that can expand a tubular member, the Amen patent does not appear to disclose an eddy current probe apparatus capable of detecting the location of a tube sheet or support plate and capable of detecting the extent of diametrical expansion of the tubular member.

Yet another device for expanding tubular members is disclosed by U.S. Pat. No. 4,513,506 issued Apr. 30, 1985 in the name of John P. Vogeleer entitled "Measuring of Tue Expansion" and assigned to the Westinghouse Electric Corporation. The Vogeleer patent is directed towards measurement of the expansion of the tubes or sleeves in tubes of a steam generator of a nuclear reactor plant. The expansion is produced by pressure of a fluid which is transmitted to the part of the tube or sleeve which is being expanded. An expansion mandrel or expander body is inserted into the tube or sleeve. A pressure fluid flows through a fluid conductor, into a channel in the mandrel and thence in contact with the tube or sleeve to be expanded. An elongated member extends through the channel and through the conductor to a position outside of the conductor. A plurality of transverse or radial captive pins or plungers extend through the mandrel between the elongated member and the tube or sleeve. Radial movement of the captive pins as the tube or sleeve is expanded produces movement of the elongated member. A dial, connected to the elongated member continuously measures the magnitude of the movement of the elongated member as the tube or sleeve is expanded. According to this patent, the expansion of the tube or sleeve as it expands is thus known and may be controlled. Although this patent discloses a device for measuring tube expansion, this patent does not appear to disclose an eddy current probe apparatus having an expansible sleeve thereon capable of diametrically expanding a tube, which probe is capable also of detecting by use of eddy currents the location of a tube sheet or support plate and the extent of diametrical expansion of the tube as provided by the present invention.

Consequently, while the prior art discloses devices for expanding tubular members, the prior art does not appear to disclose an eddy current probe apparatus for expanding a tube into engagement with a tube sheet or tube support plate, which device is capable of detecting the location of the tube sheet or support plate and also capable of detecting the extent of diametrical expansion of the tube in the manner of the present invention.

Therefore, what is needed is an eddy current probe apparatus having an expansible sleeve thereon capable of hydraulically diametrically expanding a tube into engagement with a tube sheet or tube support plate and capable of hydraulically diametrically expanding a tubular sealing member into engagement with the interior wall of the tube, which probe is also capable of detecting the location of the tube sheet or support plate and the extent of diametrical expansion of the sealing member and tube.

SUMMARY OF THE INVENTION

Disclosed herein is an eddy current probe apparatus having an expansible sleeve thereon capable of hydraulically diametrically expanding a tube into engagement with a tube sheet or tube support plate and capable of hydraulically diametrically expanding a tubular sealing member into engagement with the interior wall of the tube, which probe is capable also of detecting the location of the tube sheet or support plate and the extent of diametrical expansion of the sealing member and tube.

The eddy current probe apparatus of the present invention comprises a support body having an expansible sleeve sealingly attached to and surrounding the support body, wherein the sleeve is in fluid communication with a fluid reservoir for hydraulically diametrically expanding the sleeve into engagement with the tube so that the tube diametrically expands into engagement with the tube sheet or support plate. When the tube is expanded into engagement with the tube sheet or support plate, the gap existing between the tube and the tube sheet or between the tube and support plate is closed thereby. The sleeve is also capable of hydraulically diametrically expanding the sealing member into engagement with the tube such that the tube is suitably sleeved.

The probe apparatus further comprises an annular eddy current coil connected to the support body for detecting the variations in the electromagnetic characteristics of the tube, sealing member, tube sheet, and support plate. Thus, the eddy current coil is capable of electromagnetically detecting the location of the tube sheet or support plate relative to the eddy current coil and sleeve. In addition, the extent of diametrical expansion of the tube and sealing member is instantaneously continuously electromagnetically detected and monitored by the annular eddy current coil. Because the eddy current coil may be subjected to relatively high hydraulic pressures when the sleeve is hydraulically expanded, the eddy current coil is configured such that the eddy current coil is capable of resisting these relatively high pressures.

Therefore, one object of the present invention is to provide an eddy current probe apparatus capable of detecting the location of a tube support plate or tube sheet.

Another object of the present invention is to provide an eddy current probe apparatus capable of detecting the extent of diametrical expansion of a tubular member.

Still another object of the present invention is to provide an eddy current probe apparatus having an eddy current device capable of resisting the relatively high pressures experienced by the eddy current device in the instance when the tubular member is hydraulically expanded.

Yet another object of the present invention is to provide an eddy current probe apparatus having an expansible sleeve thereon capable of hydraulically diametrically expanding a tube into engagement with a tube sheet or tube support plate and capable of hydraulically diametrically expanding a tubular sealing member into engagement with the interior wall of the tube, which probe is capable also of detecting the location of the tube sheet or support plate and the extent of diametrical expansion of the sealing member and tube.

DESCRIPTION OF THE PREFERRED EMBODIMENT

In a nuclear reactor it is desirable that steam generator tubes remain leak-tight so that radioactive primary fluid remains everywhere separated from non-radioactive secondary fluid to avoid mingling the radioactive primary fluid with the secondary fluid. Precautionary measures may be necessary to ensure that through-wall cracking and corrosion do not occur in a tube so that the tube remains leak-tight. As described in more detail hereinafter, such precautionary measures may be to expand the tube into engagement with the tube sheet, the support plate or like structure, or to sleeve the tube.

Figure 1:
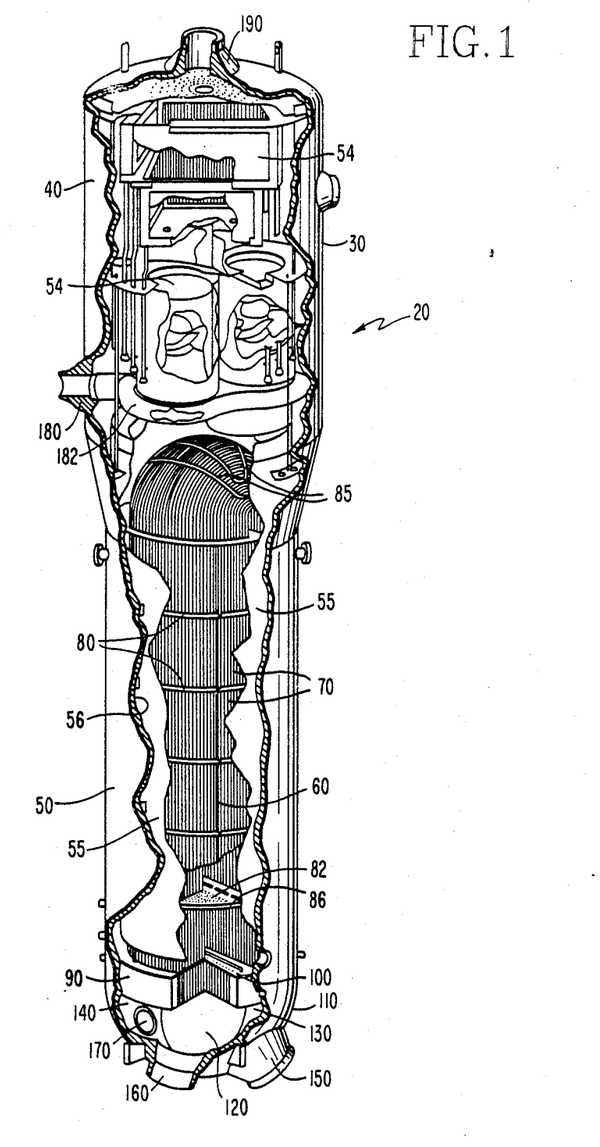
FIG. 1 shows a nuclear reactor steam generator in partial vertical section with parts removed for clarity.

Referring to FIG. 1, a steam generator is referred to generally as 20 and comprises a generally cylindrical outer shell 30 having a cylindrical upper portion 40 and a cylindrical lower portion 50. Disposed in upper portion 40 is moisture separating means 54 for separating a steam-water mixture so that entrained water is removed from the steam-water mixture. Disposed in lower portion 50 is an inner shell 55 which is closed at its top end except for a plurality of openings disposed in its top end for allowing passage of the steam-water mixture from inner shell 55 to moisture separating means 54. Inner shell 55 is open at its bottom end, which inner shell 55 defines an annulus 56 between inner shell 55 and outer shell 30. Disposed in inner shell 55 is a vertical steam generator tube bundle 60 having a plurality of vertical, U-shaped steam generator tubes 70 therein, which may be mill annealed, thermally treated Inconel 600. Disposed at various locations along the length of bundle 60 are a plurality of horizontal, circular tube support plates 80, which may be Type 405 stainless steel, having holes 82 therein for receiving each tube 70, for laterally supporting tubes 70 and for reducing flow induced vibration in tubes 70. Additional support for tubes 70 is provided in the U-bend region of bundle 60 by a plurality of anti-vibration bars 85 which may be chrome-plated Inconel.

Referring again to FIG. 1, disposed in lower portion 50 and below a bottom-most support plate 86 is a horizontal, circular tube sheet 90 having a plurality of vertical apertures 100 therethrough for receiving the ends of tubes 70 and for supporting the ends of tubes 70, which ends of tubes 70 extend a predetermined distance through apertures 100. Tube sheet 90, which may be a nickel-molybdenum-chromium-vanadium alloy clad in Inconel, is sealingly attached, which may be by welding, around its circumferential edge to a hemispherical channel head 110. Disposed in channel head 110 is a vertical, semi-circular divider plate 120 sealingly attached, which may be by welding, to channel head 110 along the circumferential edge of divider plate 120 and sealingly attached, which may be by welding, to tube sheet 90 along the flat edge of divider plate 120. Divider plate 120 divides channel head 110 into an inlet plenum chamber 130 and an outlet plenum chamber 140.

Still referring to FIG. 1, disposed on outer shell 30 below tube sheet 90 are a first inlet nozzle 150 and a first outlet nozzle 160 in fluid communication with inlet plenum chamber 130 and with outlet plenum chamber 140, respectively. A plurality of manway holes 170 are disposed on outer shell 30 below tube sheet 90 for providing access to inlet plenum chamber 130 and outlet plenum chamber 140. Disposed on outer shell 30 above tube bundle 60 is a second inlet nozzle 180, which is connected to a perforated, horizontal and generally toroidal feedring 182 disposed in upper portion 40 for allowing entry of non-radioactive secondary fluid into upper portion 40 through inlet nozzle 180 and through the perforations (not shown) of feedring 182. A second outlet nozzle 190 is disposed on the top of upper portion 40 for exit of steam from steam generator 20.

During operation of steam generator 20, radioactive primary fluid, which may be water obtaining a temperature of approximately 620 degrees Fahrenheit, enters inlet plenum chamber 130 through first inlet nozzle 150 and flows through tubes 70 to outlet plenum chamber 140 where the primary fluid exits steam generator 20 through first outlet nozzle 160. Non-radioactive secondary fluid, which may be water, enters feedring 182 through second inlet nozzle 180, which is in fluid communication with feedring 182, and flows downwardly from the perforations of feedring 182 through annulus 56 until the secondary fluid is in fluid communication with tube sheet 90. The secondary fluid then leaves annulus 56 flowing upwardly by natural convection through bundle 60 where the secondary fluid boils and vaporizes into a steam-water mixture due to conductive heat transfer from the primary fluid to the secondary fluid through the walls of tubes 70 which comprise bundle 60 and which function as heat conductors. The steam-water mixture flows upwardly from bundle 60 and is separated by moisture separating means 54 into saturated water and dry saturated steam which may obtain a minimum quality of approximately 99.75 percent. The saturated water flows downwardly from moisture separating means 54 and mixes with the secondary fluid flowing downwardly from feedring 182. Thus, as the secondary fluid enters feedring 182 through second inlet nozzle 180, dry saturated steam exits steam generator 20 through second outlet nozzle 190. In a manner well known in the art of nuclear power production, the dry saturated steam is ultimately transported to a heat sink (not shown) after the dry saturated steam exits steam generator 20 through second outlet nozzle 190. Moreover, in a nuclear reactor the primary fluid is radioactive; therefore, steam generator 20 is designed such that the radioactive primary fluid is nowhere in direct fluid communication with the non-radioactive secondary fluid in order that the secondary fluid is not radioactively contaminated by mingling with the primary fluid.

FIRST EMBODIMENT OF THE INVENTION

Figure 2:
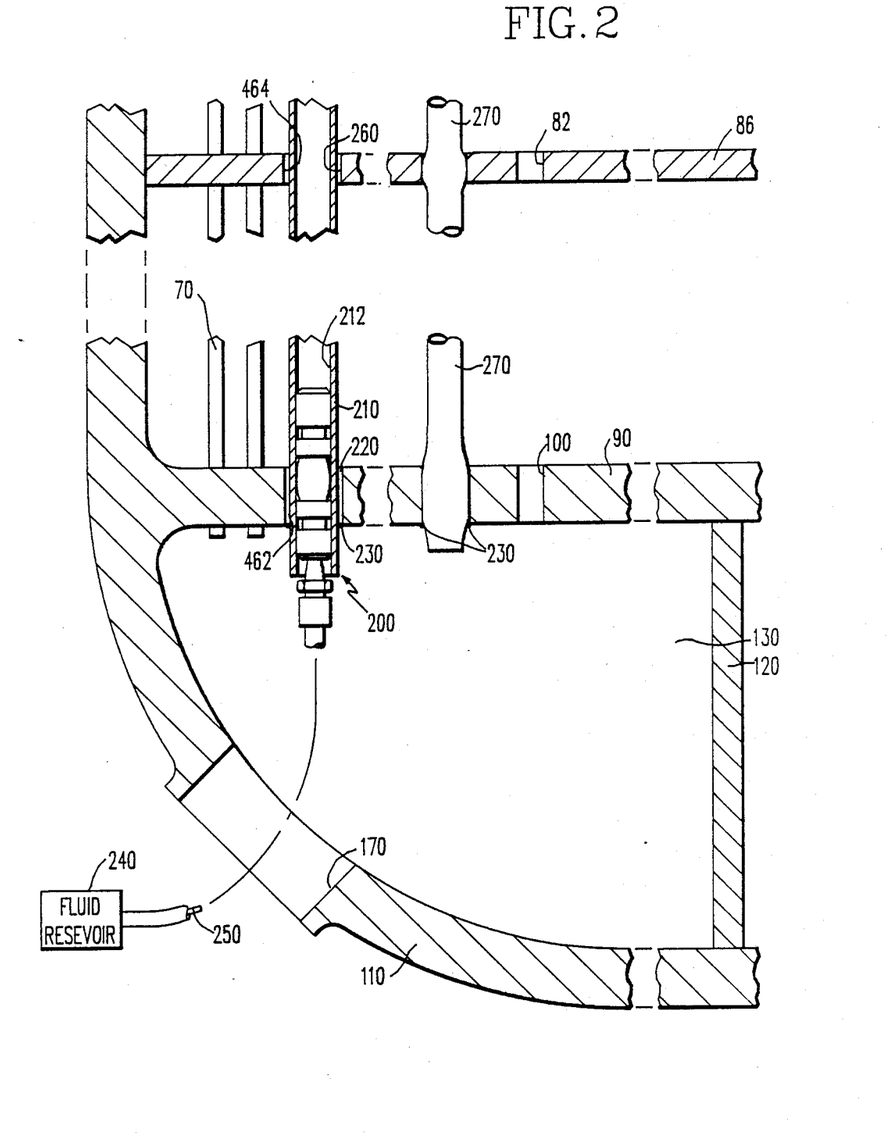
FIG. 2 is an illustration in vertical section of an inlet plenum of the steam generator showing a tube sheet and showing a support plate disposed above the tube sheet.

Turning now to FIG. 2, there is illustrated the first embodiment of the present invention, which is an eddy current probe apparatus generally referred to as 200 operatively disposed in a steam generator tube 210 having an interior wall 212, which tube 210 is to be hydraulically diametrically expanded into engagement with tube sheet 90 for closing a gap 220 existing between tube 210 and tube sheet 90. Closing gap 220 mitigates vibration of tube 210 against tube sheet 90 and deposition of contaminates within gap 220, which vibration and deposition of contaminates might otherwise cause surface and volume flaws to develop in tube 210. It will be understood that tube 210 is any one of tubes 70, the plurality of which tubes 70 comprise tube bundle 60. Tube 210, which is received through aperture 100, is attached to tube sheet 90 by a weldment 230 which secures tube 210 within aperture 100. As shown in FIG. 2, probe apparatus 200 may be in fluid communication with a fluid reservoir 240 having fluid, such as water, or gas therein and having a fluid feed conduit 250 connected thereto, which fluid feed conduit 250 extends from fluid reservoir 240 to probe apparatus 200 for supplying fluid to probe apparatus 200 so that probe apparatus 200 is capable of hydraulically diametrically expanding tube 210 into engagement with tube sheet 90.

Referring again to FIG. 2, each tube 70, including tube 210, also extends through an associated hole 82 which is formed through each support plate 86. It will be appreciated that probe apparatus 200 may be suitably translated in tube 210 to a location adjacent support plate 86 for hydraulically diametrically expanding tube 210 into engagement with support plate 86 so that a crevice 260 existing between tube 210 and support plate 86 is closed in a manner similar to the manner of closing gap 220. Probe apparatus 200 may be suitably translated in tube 210 by a suitable probe drive apparatus such as that described in U.S. Pat. No. 4,087,748 entitled "Pneumatic Drive Device for a Probe, Particularly an Eddy Current Measuring Probe" and issued in the name of Michel Pigeon et al., the disclosure of which is hereby incorporated by reference. Also illustrated in FIG. 2 is a steam generator tube 270 which has been expanded by the present invention into engagement with tube sheet 90 and support plate 86 for closing gap 220 and crevice 260, respectively.

Figure 3:
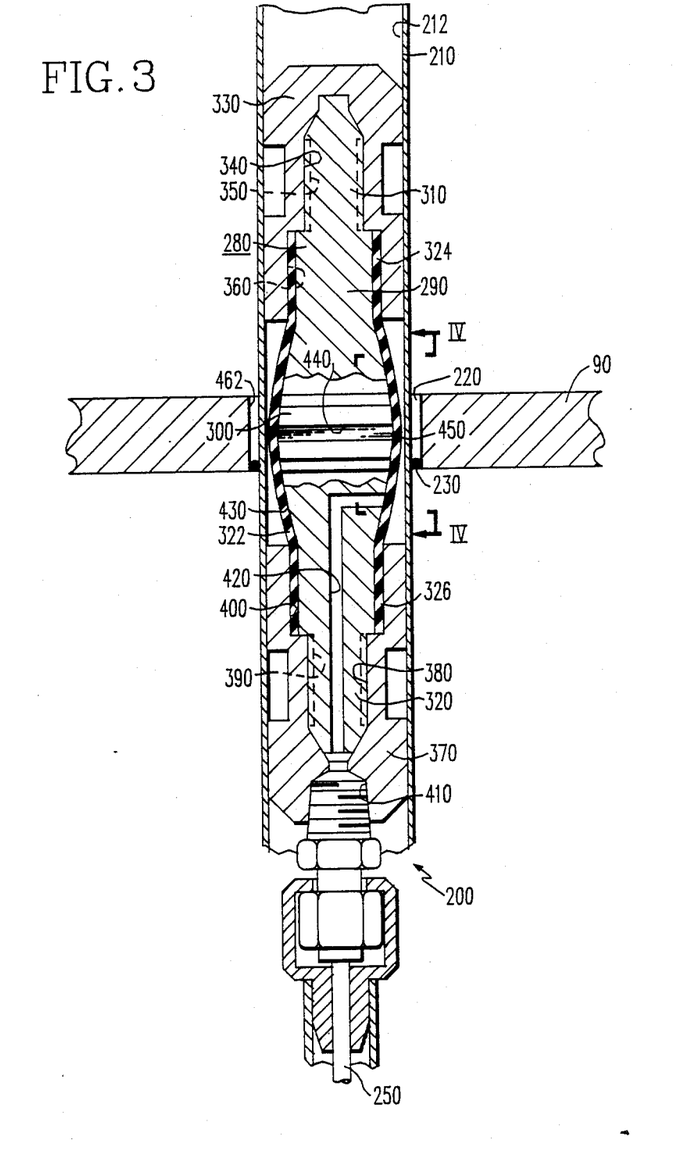
FIG. 3 shows a first embodiment of an eddy current probe apparatus which includes one eddy current coil and which is disposed in a steam generator tube.

Referring to FIG. 3, probe apparatus 200 is shown disposed in tube 210 for hydraulically diametrically expanding tube 210 into engagement with tube sheet 90 for closing gap 220 which exits between tube sheet 90 and tube 210. Probe apparatus 200 includes a generally cylindrical support body, generally referred to as 280. Support body 280 comprises an elongated generally cylindrical stud 290, which may have a bulged portion 300 of larger diameter at or near the middle portion thereof. Coaxially integrally formed at one end of stud 290 is a generally cylindrical externally threaded first stud end 310, which may be of smaller diameter. Coaxially integrally formed at the other end of stud 290 is a generally cylindrical externally threaded second stud end 320 which may be of the same diameter as first stud end 310. As shown in FIG. 3, stud 290 may generally inwardly taper from bulged portion 300 to first stud end 310 and second stud end 320. Surrounding stud 290 is a generally cylindrical expansible sleeve 322, which may be Pellethane CPR-2103-55D available from The Upjohn Company, CPR Division, located in Torrance, Calif., for diametrically expanding tube 210 into engagement with tube sheet 90. Pellethane is a urethane elastoplastic polymer having hydrolytic stability and high performance at high and low temperatures. This material possesses chemical and solvent resistance and can be used for dynamic and load-bearing applications. It will be appreciated that sleeve 322 may be used also for diametrically expanding tube 210 into engagement with support plate 86 (see FIG. 1). When used for closing gap 220 or 260, sleeve 322 may be approximately 1.3 inches long. As described presently, sleeve 322 has a first sleeve end 324 and a second sleeve end 326 capable of being sealingly compressed against stud 290 for sealingly connecting first sleeve end 324 and second sleeve end 326 to stud 290 so that hydraulic fluid does not escape sleeve 322 when sleeve 322 is inflatably expanded into engagement with tube 210.

Referring again to FIG. 3, coaxially threadably attached to first stud end 310 is a generally cylindrical first end cap 330 having a first step bore 340 therein for threadably engaging first stud end 310 and for compressing first sleeve end 324 sealingly against stud 290. First step bore 340 has an internally threaded first smaller portion 350 for threadably engaging the external threads of first stud end 310. First step bore 340 also includes an unthreaded first larger portion 360 of larger diameter for compressing first sleeve end 324 sealingly against stud 290. Similarly, coaxially threadably attached to second stud end 320 is a generally cylindrical second end cap 370 having a second step bore 380 therein. Second step bore 380 includes an internally threaded second smaller portion 390 for threadably engaging the external threads of second stud end 320. Second step bore 380 also includes an unthreaded second larger portion 400 of larger diameter for compressing second sleeve end 326 sealingly against stud 290. First larger portion 360 and second larger portion 400 may outwardly taper from first smaller portion 350 and second smaller portion 390 of first step bore 340 and second step bore 380, respectively, for matingly compressing first sleeve end 324 and second sleeve end 326 against the associated inwardly tapering portions of stud 290. Thus, first sleeve end 324 is sealingly interposed between first larger portion 360 of first step bore 340 and stud 290 for sealingly connecting first sleeve end 324 to stud 290. Similarly, second sleeve end 326 is thus sealingly interposed between second larger portion 400 of second step bore 380 and stud 290 for sealingly connecting second sleeve end 326 to stud 290. In this manner, first sleeve end 324 and second sleeve end 326 are sealingly compressed against stud 290 so that hydraulic fluid does not escape sleeve 322 when sleeve 322 is inflatably expanded into engagement with tube 210.

Still referring to FIG. 3, second end cap 370 may include a generally frusto-conical cavity 410 therein in fluid communication with fluid feed conduit 250 at one end thereof and with second stud end 320 at the other end thereof for delivering fluid from fluid feed conduit 250 to second stud end 320. Also formed through stud 290 is a channel 420 which may extend from second stud end 320 to an external surface 430 of stud 290 on the in-board side of sleeve 322 for channeling fluid to and withdrawing fluid from sleeve 322. The fluid referred to immediately above flows from fluid feed conduit 250, through cavity 410, through channel 420, and to sleeve 322, so that sleeve 322 is hydraulically pressurized thereby. As shown in FIG. 3, channel 420 may have an inverted generally L-shaped configuration as it extends from second stud end 320 to external surface 430.

Figure 4:
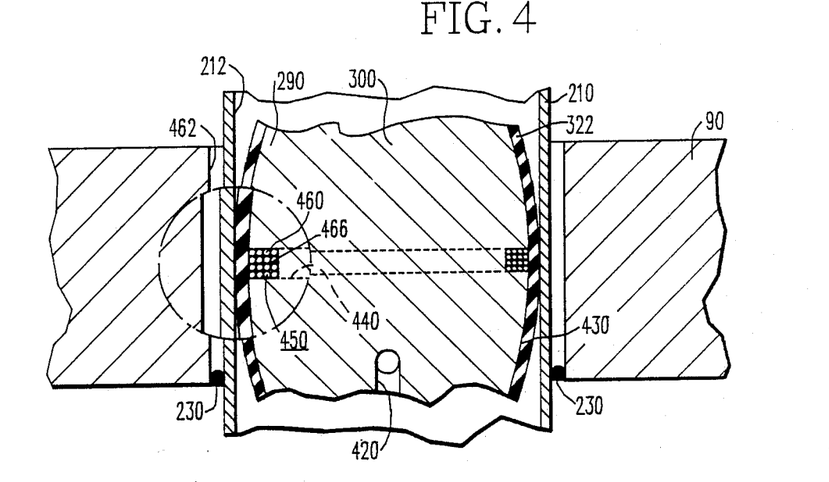
FIG. 4 is an illustration taken along section IV—IV of FIG. 3 showing an expansible sleeve surrounding a portion of the probe apparatus which includes eddy current coil wires having a round cross sectional configuration.

Referring to FIG. 4, at least one groove 440, which may have a substantially square-shaped cross-sectional configuration, is formed in stud 290 around the circumference of bulged portion 300 for matingly receiving an associated integral eddy current coil 450 therein, wherein each eddy current coil 450 may have a generally square cross-sectional configuration for matingly lodging in groove 440. Eddy current coil 450 is thereby connected to stud 290 when it is lodged in groove 440. Eddy current coil 450 includes a plurality of electricity conducting wires 460 therein, which may be copper and approximately 0.005 inch in diameter in cross-section, that surround a portion of bulged portion 300 on the in-board side of sleeve 322 for detecting the variations in the electromagnetic characteristics of tubesheet 90 or support plate 86. When eddy current coil 450 is moved in tube 210 to near tube sheet 90, eddy current coil 450 is capable of electromagnetically detecting the presence of a tube sheet inner edge 462. Similarly, when eddy current coil 450 is moved in tube 210 to near support plate 86, eddy current coil 450 is capable of electromagnetically detecting the presence of a support plate inner edge 464 (see FIG. 2). Eddy current coil 450 is thus capable of electromagnetically detecting the location of tube sheet 90 or support plate 86 relative to eddy current coil 450 and sleeve 322. Moreover, eddy current coil 450 is capable of continuously electromagnetically detecting the extent of diametrical expansion of tube 210 by inducing eddy currents in tube 210 and transmitting the variations in the eddy currents to an eddy current measuring unit (not shown).

Figure 5:
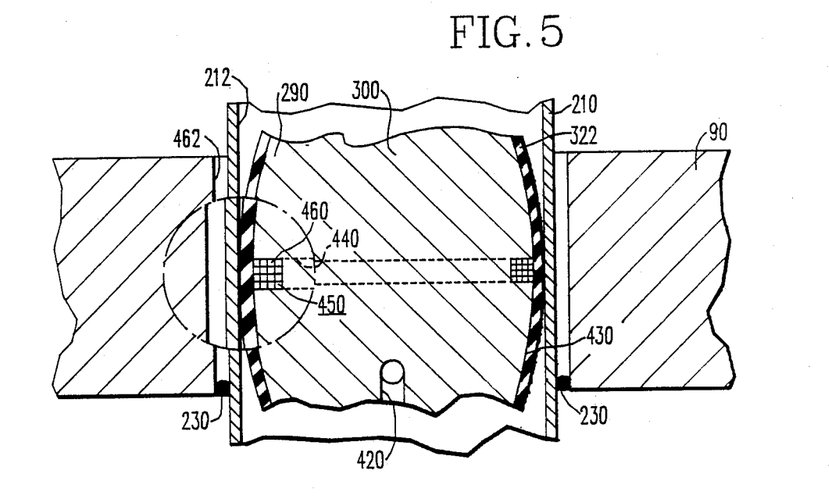
FIG. 5 illustrates the expansible sleeve surrounding a portion of the probe apparatus which includes eddy current coil wires having a square cross-sectional configuration.

Again referring to FIG. 4, each of the plurality of wires 460 obtains a round cross-sectional configuration and is relatively thin for resisting the pressurization of sleeve 322 when sleeve 322 is hydraulically expanded. The pressurization may be between approximately 12,000 and 20,000 pounds per square inch gauge. However, it will be understood that a plurality of voids 466 are defined between wires 460 when wires 460 are wound about bulged portion 300 in groove 440 and stacked adjacent one to the other. It is undesirable to obtain voids 466 in eddy current coil 450 because the fluid used to pressurize and expand sleeve 322 also may seep into voids 466 between wires 460 thereby pressurizing and expanding eddy current coil 450. Pressurization of eddy current coil 450 in this manner may cause eddy current coil 450 to catastrophically rupture or operate in a manner not intended. Thus, in the preferred embodiment (see FIG. 4) eddy current coil 450 is constructed of relatively thin wire, which may be approximately 0.005 inch in diameter, for reducing the total volume of voids 466 in eddy current coil 450. Wires 460 are arranged in an annular configuration around bulged portion 300 for continuously instantaneously electromagnetically detecting and measuring the extent of diametrical expansion of tube 210. Alternatively, the extent of diametrical expansion of tube 210 may be detected and measured by suitably detecting and measuring the change in pressure in fluid feed conduit 420. It will be appreciated that the thinner each wire 460, the smaller is the total volume of voids defined between adjacent wires 460. Alternatively, the plurality of wires 460 may be selected such that a square cross-sectional configuration (see FIG. 5) is obtained for each wire 460 for resisting the pressurization of eddy current coil 450 when sleeve 322 is hydraulically pressurized and expanded. It will be understood that the use of wires 460 each having a square cross-sectional configuration substantially eliminates voids 466.

Figure 6:
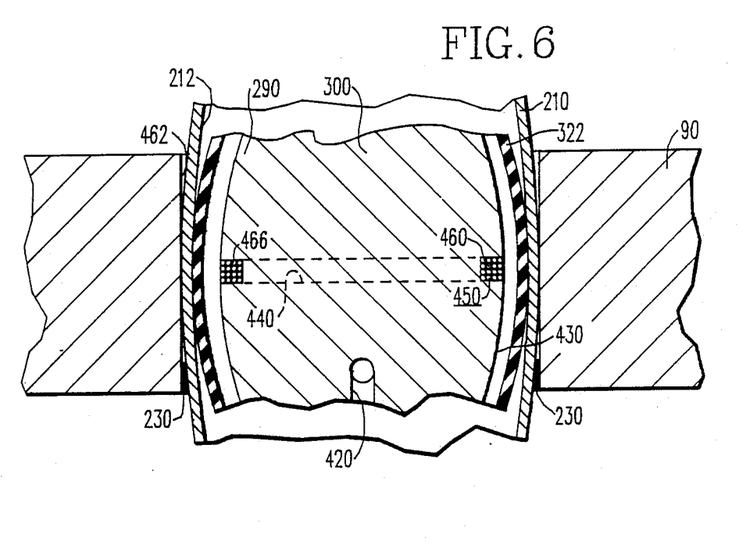
FIG. 6 is an illustration of the sleeve hydraulically expanding the tube into engagement with a tube sheet.

As shown in FIG. 6, sleeve 322 is capable of diametrically expanding when fluid, which should be transparent to eddy current waves, flows through channel 420 to sleeve 322 for pressurizing sleeve 322. When sufficiently pressurized, sleeve 322 diametrically expands into engagement with tube 210 for diametrically expanding tube 210 into engagement with tube sheet 90 or support plate 86 for closing gap 220 or gap 260, respectively. It will be appreciated that as tube 210 is expanded a predetermined radial distance beyond its elastic limit, tube 210 becomes permanently deformed. The extent of diametrical expansion of sleeve 322 and the extent of diametrical expansion of tube 210 are controlled such that tube 210 expands only to a predetermined radial distance. As described hereinabove, eddy current coil 450 is capable of detecting, by its annular configuration, the extent of diametrical expansion of tube 210 by detecting the variations in the electromagnetic field induced in tube 210 as tube 210 diametrically expands. Of course, eddy current coil 450 is electronically connected to a suitable display device or eddy current measuring unit (not shown) chosen from those commonly available in the art for detecting, monitoring, measuring and displaying the electrical signals from eddy current coil 450. Eddy current coil 450 is also electronically connected to an electrical supply (not shown) for supplying electricity to eddy current coil 450 so that eddy current coil 450 is capable of inducing eddy currents in an adjacent structure.

Figure 7:
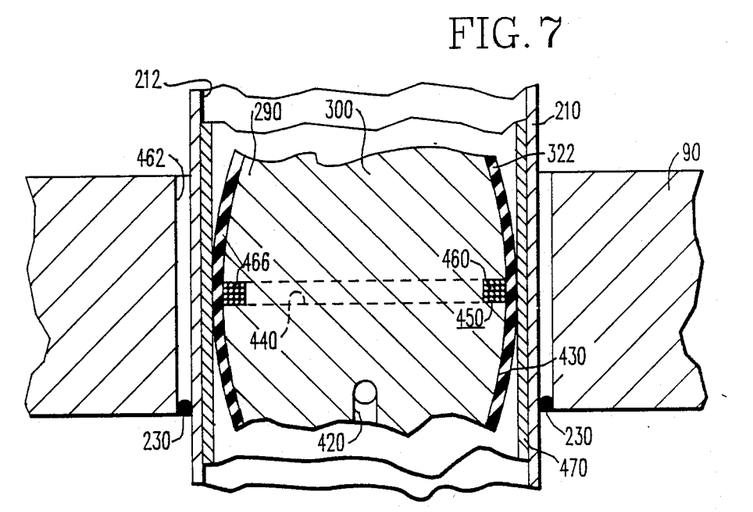
FIG. 7 shows the expansible sleeve in operative condition for diametrically expanding a tubular sealing member into engagement with the tube for sleeving the tube.

If tube 210 has surface and volume flaws, tube 210 may not remain leak-tight because tube 210 may leak and rupture due to the flaws thereby causing the radioactive primary fluid to mingle with the non-radioactive secondary fluid surrounding tube 210. A typical practice in the art, commonly referred to as sleeving, is to dispose another tube within tube 210 so that radioactive primary fluid can not mingle with the non-radioactive secondary fluid. Therefore, referring to FIG. 7, coaxially disposed in tube 210 is a tubular sealing member 470 for sealing tube 210 by sleeving tube 210 so that sealing member 470 presents a barrier within tube 210 between the primary fluid flowing in tube 210 and the secondary fluid flowing externally around tube 210 and so that sealing member 470 structurally seals and reinforces tube 210 in the region of the flaws. In this manner, primary fluid can not mingle with the secondary fluid when tube 210 has surface and volume flaws because sealing member 470 defines a barrier within tube 210 between the primary fluid and the secondary fluid for preventing the mingling of primary and secondary fluids. However, in order to suitably sleeve tube 210, sealing member 470 should be diametrically expanded into engagement with tube 210. As described presently, probe apparatus 200 is capable of diametrically expanding sealing member 470 into sealing engagement with tube 210 such that tube 210 is suitably sleeved.

Figure 8:
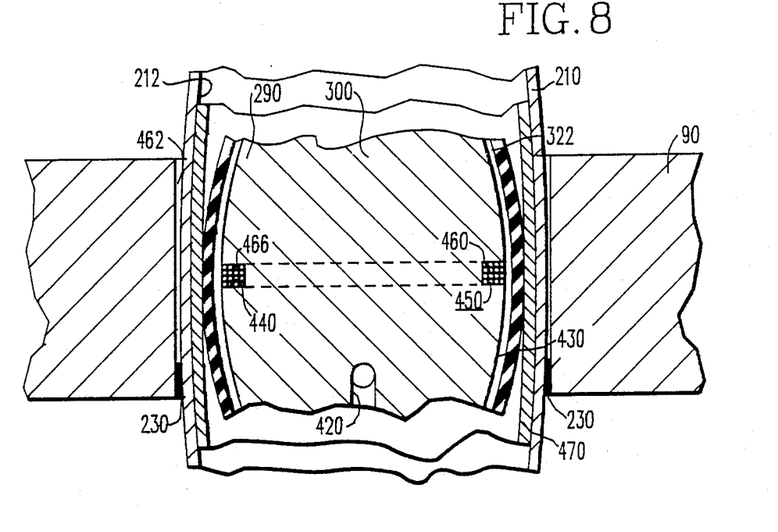
FIG. 8 illustrates in vertical section the sleeve outwardly expanding the sealing member into engagement with the tube.

Referring to FIG. 8, expansible sleeve 322 is shown diametrically expansibly engaging sealing member 470 such that sealing member 470 diametrically expansibly engages tube 210 for sleeving tube 210. When used for sleeving, expansible sleeve 322 may be approximately 4 inches long. When sealing member 470 diametrically expands, tube 210 diametrically expands to like extent due to the diametric force of expansion radially exerted by sealing member 470 against tube 210 as sealing member 470 diametrically expands into engagement with tube 210. It will be appreciated that sealing member 470 and tube 210 are expanded a predetermined radial distance beyond their respective elastic limits so that sealing member 470 and tube 210 are permanently deformed after the expansion process is completed.

As described hereinabove, tube 210 may have surface and volume flaws; hence, diametrical expansion of tube 210 excessively beyond its elastic limit may cause tube 210 to catastrophically rupture. Therefore, the extent of diametrical expansion of sleeve 322 and hence the extent of diametrical expansion of sealing member 470 are controlled such that sealing member 470 and tube 210 diametrically expand and deform only to a predetermined radial distance sufficient to avoid catastrophic rupture of tube 210. The extent of diametrical expansion of tube 210 and sealing member 470 are detected by instantaneously and continuously monitoring and measuring the variations in the electromagnetic field induced in sealing member 470 and tube 210 by eddy current coil 450. Alternatively, the extent of diametrical expansion of sealing member 470 and tube 210 may be monitored and measured by suitably monitoring and measuring the change in fluid pressure in fluid feed conduit 420. When sealing member 470 and tube 210 expand a predetermined radial distance, the hydraulic fluid flowing through channel 420 to sleeve 322 is withdrawn from sleeve 322, thereby depressurizing sleeve 322 and deflating sleeve 322, such that sleeve 322 no longer expansibly diametrically engages sealing member 470.

The change in fluid pressure as a function of time in fluid feed conduit 420 may be suitably monitored and measured with the aid of a hydraulic expansion unit (not shown) such as HYDROSWAGE brand hydraulic expander manufactured by Haskel, Inc. of Burbank, Calif. This expansion unit includes a low pressure supply system and pressure intensifier, a control box for controlling the operation of the pressure intensifier, and a solenoid valve capable of controlling the flow of hydraulic fluid from the pressure intensifier to sleeve 322 via feed conduit 420. The pressure intensifier may be controlled, via the control box, by a tube expansion control circuit (not shown) which operates in conjunction with a pressure transducer (not shown). The pressure transducer is in turn fluidly connected to the outlet of the pressure intensifier and electrically connected to the expansion control circuit. The control circuit is capable of raising the hydraulic pressure acting against tube 210 or sealing member 470 by a predetermined percentage above the contact pressure after full contact has been made with tube sheet 90 or tube 210, respectively. Thus, the hydraulic expansion unit acting in cooperation with the tube expansion control circuit is capable of monitoring and measuring the hydraulic pressure as a function of time during the expansion process such that leaks or over-pressure conditions which could over-expand tube 210 and/or sealing member 470 are detectable.

SECOND EMBODIMENT OF THE INVENTION

Figure 9:
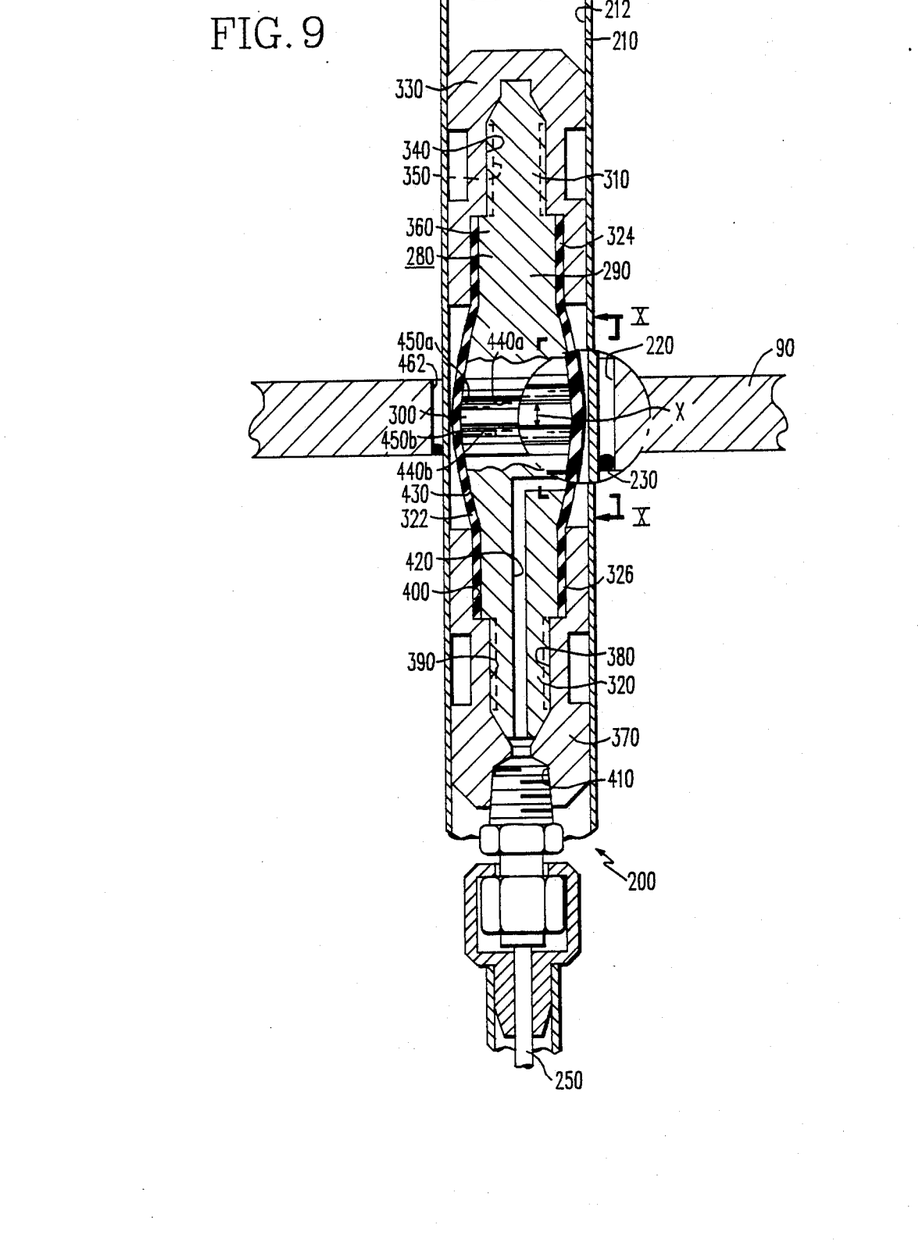
FIG. 9 shows a second embodiment of the eddy current probe apparatus which includes two eddy current coils.
Figure 10:
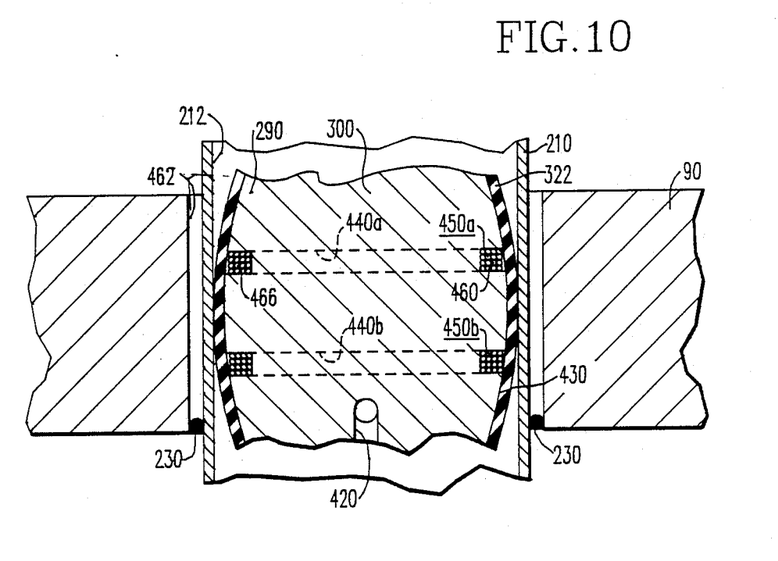
FIG. 10 is an illustration taken along section X—X of FIG. 9 showing the cross-sectional configuration of each eddy current coil.

FIGS. 9 and 10 illustrate the second embodiment of the present invention. As shown in FIGS. 9 and 10, the second embodiment of the invention differs from the first embodiment at least with respect to the number of eddy current coils 450$a$ and 450$b$ and associated grooves 440$a$ and 440$b$. As shown in FIGS. 9 and 10, two eddy current coils 450$a$ and 450$b$ are each wound in an associated groove 440$a$ and 440$b$, respectively. Eddy current coils 450$a$ and 450$b$ are separated by a predetermined longitudinal distance- X and, as similar to the first embodiment, are interposed between sleeve 322 and bulged portion 300. As will be described in more detail hereinafter, increasing the number of eddy current coils 450 to two increases the accuracy of determining the location of support plate 86.

In the second embodiment, the outside edges of eddy current coils 450$a$ and 450$b$ along the longitudinal axis of stud 90 are spaced at approximately the same distance as the width of support plate 86, which may be approximately 0.75 inch wide, so that the eddy current coils 450$a$ and 450$b$; may detect with precision the location of support plate 86 with respect to the longitudinal axis of tube 210. When eddy current coils 450$a$ and 450$b$ are connected to conventional eddy current probe circuitry, such coil spacing yields a lissajous curve with a point intersection whenever the longitudinal edges of eddy current coils 450$a$ and 450$b$ are flush with the top and bottom edges of support plate 86. It will be understood that the spacing X of eddy current coils 450$a$ and 450$b$ does not interfere with the use of eddy current coils 450$a$ and 450$b$ for detecting defects or deposits along the walls of tube 210. In addition, when tube 210 is sleeved, an interference joint is formed at the interface of sealing member 470 and tube 210 when sealing member 470 expansibly engages tube 210. Therefore, it will be understood that spacing of eddy current coils 450$a$ and 450$b$ does not interfere with the use of eddy current coils 450$a$ and 450$b$ for mapping the profile of the interference joint which is formed when sealing member 470 expansibly engages tube 210.

When probe apparatus 200 is used to close gap 220 existing between tube sheet 90 and tube 210 or to close gap 260 existing between support plate 86 and tube 210, probe apparatus 200 is translated in tube 210 by operating a suitable probe drive apparatus (not shown) which is connected to probe apparatus 200 and which may be selected from those well known in the art of non-destructive examination. Probe apparatus 200 is translated in tube 210 to a predetermined location at or near tube sheet 90 or support plate 86 for closing gap 220 or gap 260, respectively. The location of tube sheet 90 or support plate 86 is detected by eddy current coil 450, as described hereinabove, when eddy current coil 450 is at or near tube sheet 90 or support plate 86 and when eddy current coil 450 induces an electromagnetic field in tube sheet 90 or support plate 86. When probe apparatus 200 reaches its predetermined location at or near tube sheet 90 or support plate 86, hydraulic fluid is caused to flow from fluid reservoir 240, through fluid feed conduit 250, through cavity 410, to second stud end 320, through channel 420 and to sleeve 322 for pressurizing sleeve 322 and thusly diametrically expanding sleeve 322. As sleeve 322 diametrically expands, sleeve 322 diametrically expansibly engages tube 210, thereby exerting a diametrical force of expansion against tube 210 until tube 210 diametrically outwardly expands beyond its elastic limit into engagement with tube sheet 90 or support plate 86 for permanently closing gap 220 or gap 260, respectively. The diametrical expansion of tube 210 is suitably continuously instantaneously monitored by eddy current coil 450, as specified hereinabove, so that tube 210 is diametrically expanded only to a predetermined radial extent. When tube 210 is expanded to the predetermined radial distance, the hydraulic fluid is suitably withdrawn from sleeve 322, through channel 420, to second stud end 320, through cavity 410, through fluid feed conduit 250, and into fluid reservoir 240 such that sleeve 322 no longer hydraulically expansibly diametrically engages tube 210. When the expansion process for closing gap 220 or 260 described immediately above is completed, probe apparatus 200 is suitably translated out of tube 210 by suitably operating the probe drive apparatus connected to probe apparatus 200.

On the other hand, when probe apparatus 200 is used to sleeve tube 210, probe apparatus 200 is translated to a predetermined location in sealing member 470, which is disposed in tube 210 opposite that portion of tube 210 having flaws, by suitably operating the probe drive apparatus which is connected to probe apparatus 200. Probe apparatus 200 is thus translated in sealing member 470 to the predetermined location which may be at that portion of tube 210 having flaws. When probe apparatus 200 reaches its predetermined location, hydraulic fluid is caused to flow from fluid reservoir 240, through fluid feed conduit 250, through cavity 410, to second stud end 320, through channel 520 and to sleeve 322 for pressurizing sleeve 322 and thusly diametrically expanding sleeve 322. As sleeve 322 diametrically expands, sleeve 322 expansibly diametrically engages sealing member 470 which is disposed in tube 210, thereby exerting a diametrical force of expansion against sealing member 470 sufficient to cause sealing member 470 to diametrically expand into sealing engagement with tube 210 for sleeving tube 210. The diametrical expansion of tube 210 is monitored by eddy current coil 450 in the manner described above so that tube 210 diametrically expands only by a predetermined radial extent. The annular configuration of wires 460 comprising eddy current coil 450 allows eddy current coil 450 to instantaneously continuously monitor the diametrical expansion of sealing member 470 and tube 210. After sealing member 470 and tube 210 are expanded the predetermined radial distance, the hydraulic fluid is suitably withdrawn from sleeve 322, through channel 420, to second stud end 320, through cavity 410, through fluid feed conduit 250, and into fluid reservoir 240 such that sleeve 322 no longer hydraulically expansibly diametrically engages sealing member 470. When the sleeving process described immediately above is completed, probe apparatus 200 is suitably translated out of sealing member 470 by suitably operating the probe drive apparatus connected to probe apparatus 200.

Of course, it will be understood that modifications and variations may be effected without departing from the spirit and scope of the novel concepts of the present invention.

Therefore, this invention provides an eddy current probe apparatus having an expansible sleeve thereon capable of hydraulically diametrically expanding a tube into engagement with a tube sheet or tube support plate and capable of hydraulically diametrically expanding a tubular sealing member into engagement with the interior wall of the tube, which probe is also capable of detecting the location of the tube sheet or support plate and the extent of diametrical expansion of the sealing member and tube.

What is claimed is:

1. An eddy current probe apparatus capable of being disposed in a tubular member adjacent to a structure, comprising:
   (a) a support body disposed in the tubular member;
   (b) expansion means sealingly attached to and surrounding said support body for diametrically expanding the tubular member into engagement with the structure; and
   (c) electromagnetic means connected to said support body and interposed between said support body and said expansion means for detecting the variations in the electromagnetic characteristics of the tubular member and of the structure, whereby the location of the structure relative to said expansion means is electromagnetically detected thereby and whereby the extent of diametrical expansion of the tubular member is continuously electromagnetically detected by said electromagnetic means.

2. The apparatus according to claim 1, further comprising fluid feed means in fluid communication with said expansion means for pressurizing and depressurizing said expansion means.

3. The apparatus according to claim 2, wherein said electromagnetic means further comprises an eddy current coil connected to and surrounding said support body.

4. The apparatus according to claim 3, wherein said electromagnetic means further comprises a plurality of thin electricity-conducting wires each having a round cross-sectional configuration.

5. The apparatus according to claim 4, wherein said wires are arranged in an annular configuration surrounding said support body for continuously electromagnetically detecting the extent of diametrical expansion of the tubular member.

6. The apparatus according to claim 3, wherein said eddy current coil further comprises a plurality of electricity-conducting wires each having a square cross sectional configuration for resisting the pressurization of said eddy current coil.

7. The apparatus according to claim 6, wherein said wires are arranged in an annular configuration surrounding said support body for continuously electromagnetically detecting the extent of diametrical expansion of the tubular member.

8. In a nuclear reactor power plant, an eddy current probe apparatus capable of being disposed in a steam generator tube adjacent to a structure, comprising:
   (a) a generally cylindrical support body capable of being disposed in the tube;
   (b) a generally cylindrical expansible sleeve surrounding said support body for diametrically expanding the tube into engagement with the structure, said sleeve having a first sleeve end and a second sleeve end capable of being sealingly compressed against said support body;
(c) fluid feed means in fluid communication with said sleeve for pressurizing and depressurizing said sleeve;
(d) an eddy current coil connected to said support body and interposed between said support body and said sleeve and having a plurality of electricity conducting wires therein surrounding said support body on the in-board side of said sleeve for detecting the variations in the electromagnetic characteristics of the tube and of the structure, whereby the location of the structure relative to said sleeve is electromagnetically detected thereby and whereby the extent of diametrical expansion of the tube is continuously electromagnetically detected by said eddy current coil.

9. The apparatus according to claim 8, wherein said wires have a square cross-sectional configuration for resisting the pressurization of said eddy current coil.

10. The apparatus according to claim 9, wherein said wires are arranged in an annular configuration around said support body for continuously electromagnetically detecting the extent of diametrical expansion of the tube.

11. The apparatus according to claim 10, wherein said support body further comprises:
(a) a generally cylindrical stud having an externally threaded first stud end and an externally threaded second stud end and having an external surface thereon;
(b) a generally cylindrical first end cap coaxially threadably attached to the first stud end, said first end cap having a first step bore therein having internal threads in the smaller portion thereof for threadably engaging the external threads of the first stud end and having a smoother surface in the larger portion thereof for sealingly compressing the first sleeve end of said sleeve against said stud;
(c) a generally cylindrical second end cap coaxially threadably attached to the second stud end, said second end cap having a second step bore therethrough having internal threads in the smaller portion thereof for threadably engaging the external threads of the second stud end and having a smoother surface in the larger portion thereof for sealingly compressing the second sleeve end of said sleeve against said stud, said second end cap having a cavity therein in fluid communication with the second stud end at one end of the cavity and with said fluid feed means at the other end of the cavity for delivering fluid from said fluid feed means to the second stud end; and
(d) a channel formed through said stud and extending from the second stud end to the external surface of said stud opposite said sleeve for channeling fluid to and withdrawing fluid from said sleeve, whereby said sleeve is pressurized and depressurized thereby.

12. The apparatus according to claim 11, wherein said fluid feed means further comprises a fluid feed conduit extending from a fluid supply reservoir to the second step bore for supplying fluid to the channel, whereby said sleeve surrounding said stud is expansibly pressurized when fluid flows from the fluid supply reservoir, through said fluid feed conduit, through the cavity, to the second stud end, through the channel and to the sleeve for pressurizing said sleeve.

13. The apparatus according to claim 12, wherein said stud has a circumferentially bulged portion near the middle portion thereof for decreasing the radial diametrical distance of expansion of said sleeve when said sleeve expands into engagement with the tube.

14. The apparatus according to claim 13, wherein said bulged portion has a circumferential groove therein having a square cross-sectional configuration for receiving said eddy current coil flush within the groove.

* * * * *